United States Patent
Tiedje (10) Patent No.: US 10,022,512 B2
(45) Date of Patent: Jul. 17, 2018

(54) SYSTEM AND METHOD FOR SYNCHRONIZATION OF BREATHING IN A MECHANICAL VENTILATOR

(71) Applicant: BREAS MEDICAL AB, Mölnlycke (SE)

(72) Inventor: Mikael Tiedje, Hisings-Kärra (SE)

(73) Assignee: Breas Medical AB, Mölnlycke (SE)

(*) Notice: Subject to any disclaimer, the term of this patent is extended or adjusted under 35 U.S.C. 154(b) by 506 days.

(21) Appl. No.: 14/771,640

(22) PCT Filed: Nov. 5, 2013

(86) PCT No.: PCT/SE2013/051293
§ 371 (c)(1),
(2) Date: Aug. 31, 2015

(87) PCT Pub. No.: WO2014/133430
PCT Pub. Date: Sep. 4, 2014

(65) Prior Publication Data
US 2016/0008559 A1  Jan. 14, 2016

Related U.S. Application Data (60) Provisional application No. 61/771,095, filed on Mar. 1, 2013.

(51) Int. Cl.
*A61B 5/00* (2006.01)
*A61B 5/0205* (2006.01)
(Continued)

(52) U.S. Cl.
CPC ....... *A61M 16/0003* (2014.02); *A61B 5/0205* (2013.01); *A61B 5/087* (2013.01);
(Continued)

(58) Field of Classification Search
CPC .............. A61M 16/00; A61M 16/0003; A61M 16/0051; A61M 16/0069;
(Continued)

(56) References Cited

U.S. PATENT DOCUMENTS 5,513,631 A * 5/1996 McWilliams ....... A61M 16/024
128/204.23
2004/0050387 A1 3/2004 Younes
(Continued)

FOREIGN PATENT DOCUMENTS

| WO | WO 02/28460 A1 | 4/2002 |
| WO | WO-2006/005433 A1 | 1/2006 |
| WO | WO-2009/149351 A1 | 12/2009 |

OTHER PUBLICATIONS

International Search Report and Written Opinion dated Mar. 3, 2015 for PCT Application No. PCT/SE2013/051293.

*Primary Examiner* — Jennifer M Deichl
(74) *Attorney, Agent, or Firm* — Ascentage Patent Law, LLC; Travis Lee Johnson; David S. Einfeldt (57) ABSTRACT

Example embodiments presented herein are directed towards a system, and corresponding method, for providing ventilation synchronization between breathing gas supplied by a mechanical ventilator and the breathing needs of a patient. In providing the ventilation synchronization, a total amount of energy required during an inspiratory phase of breathing is calculated. Based on the calculated energy, a decay factor is determined. The decay factor is supplied to an inspiratory triggering system in order to provide the ventilation synchronization.

29 Claims, 3 Drawing Sheets

(51) Int. Cl.
    *A61B 5/0402*  (2006.01)
    *A61B 5/08*    (2006.01)
    *A61B 5/087*   (2006.01)
    *A61B 5/113*   (2006.01)
    *A61B 5/145*   (2006.01)
    *A61M 16/00*   (2006.01)
    *A61M 16/10*   (2006.01)

(52) U.S. Cl.
    CPC .......... *A61B 5/113* (2013.01); *A61B 5/14542* (2013.01); *A61B 5/4836* (2013.01); *A61M 16/0051* (2013.01); *A61B 5/0402* (2013.01); *A61B 5/082* (2013.01); *A61M 2016/0027* (2013.01); *A61M 2016/0039* (2013.01); *A61M 2016/103* (2013.01); *A61M 2016/1025* (2013.01); *A61M 2205/3368* (2013.01); *A61M 2205/3375* (2013.01); *A61M 2230/005* (2013.01); *A61M 2230/04* (2013.01); *A61M 2230/10* (2013.01); *A61M 2230/14* (2013.01); *A61M 2230/18* (2013.01); *A61M 2230/205* (2013.01); *A61M 2230/30* (2013.01); *A61M 2230/42* (2013.01); *A61M 2230/432* (2013.01); *A61M 2230/435* (2013.01); *A61M 2230/50* (2013.01); *A61M 2230/60* (2013.01)

(58) Field of Classification Search
    CPC .......................... A61M 16/022–16/024; A61M 2016/0015–2016/0042; A61B 5/087; A61B 5/113
    See application file for complete search history.

(56) References Cited

U.S. PATENT DOCUMENTS

| | | | | |
|---|---|---|---|---|
| 2008/0283061 | A1* | 11/2008 | Tiedje | A61M 16/0051 128/204.23 |
| 2008/0295839 | A1* | 12/2008 | Habashi | A61M 16/0051 128/204.22 |
| 2014/0290658 | A1* | 10/2014 | Schindhelm | A61M 16/0051 128/204.23 |

* cited by examiner

SYSTEM AND METHOD FOR SYNCHRONIZATION OF BREATHING IN A MECHANICAL VENTILATOR

TECHNICAL FIELD

Example embodiments presented herein relate to providing synchronization of breathing cycles between a breathing gas supplied by a mechanical ventilator and a patient's needs.

BACKGROUND

Patients suffering from different forms of breathing disorders can be subject to several types of treatments depending on the illness or disorder present. One form of treatment is to use a mechanical ventilator as it represents a non-invasive technique for the treatment of certain breathing disorders such as ventilatory failure, hypoventilation, periodic breathing during sleep and wakefulness, and in sleep apnea that occurs exclusively during sleep.

Ventilatory failure comprises all forms of insufficient ventilation with respect to a metabolic need which may occur during wakefulness or periods of sleep. Hypoventilation and periodic breathing, in its most frequently occurring form referred to as Cheyne-Stokes ventilation, may occur periodically or constantly during wakefulness or sleep. Conditions associated with hypoventilation, in particular nocturnal hypoventilation, may comprise, for example, central nervous system disorders such as stroke, muscular dystrophies, certain congenital conditions, advanced chronic obstructive pulmonary disease (COPD), etc. Cheyne-Stokes ventilation or various forms of central apnea are commonly associated with cardiac and circulatory disorders, in particular cardiac failure.

Ventilatory failure is a potentially life threatening condition. The general comorbidity in patients with failing ventilation is considerable. The condition is highly disabling in terms of reduced physical capacity, cognitive dysfunction in severe cases and poor quality of life. Patients with ventilatory failure therefore experience significant daytime symptoms but in addition, the majority of these cases experience a general worsening of their condition during state changes such as sleep. The phenomenon of disordered breathing during sleep, whether occurring as a consequence of ventilatory failure or as a component of sleep apnea in accordance with the description above causes sleep fragmentation. Daytime complications include sleepiness and cognitive dysfunction. Severe sleep disordered breathing occurring in other comorbid conditions like obesity, neuromuscular disease, post polio myelitis states, scoliosis or heart failure may be associated with considerable worsening of hypoventilation and a compromised blood gas balance. Sleep apnea has been associated with cardiovascular complications such as, for example, coronary heart disease, myocardial infarction, stroke, arterial hypertension, thrombosis, and cardiac arrhythmia. It is therefore of both immediate and long-term interest to reduce the exposure to sleep disordered breathing.

In ventilation treatment it is crucial that the inspiratory and expiratory phases of the applied system synchronize with the patient's own ventilation efforts. A system that does not comply with patient effort creates an air trapping situation and increases discomfort as well as a considerably increased anxiety for the patient. Several different systems have been developed to make mechanical ventilators operate in accordance with patient rhythms. The key component in such systems is the ability to sense the patient's rhythm or breathing phases. The early systems used pressure sensing devices to detect the pressure drop when a patient tried to inhale.

Flow systems, which succeeded the pressure systems, were based on a flow sensing mechanism which sensed the flow of gas entering and leaving the patient. There have been a number of methods of measuring the instantaneous and average gas flow described in literature to calculate the inspiratory and expiratory triggering points.

SUMMARY

Various problems exist with current synchronization methods. With respect to synchronization methods based on the sensing of a patient's breathing rhythm, these systems led to the patient having to make a higher effort due to the fact that a breathing tube needs to be de-pressurized before the trigger detection may be made. One of the major problems in flow based mechanisms is that the system has to calculate the actual leakage from mask, mouth, and other leakages in the breathing circuits. The leakage detection may lead to machine induced inspiratory triggering problems and missed inspiratory triggers. If a missed inspiratory trigger occurs it will result in the ventilator not responding to patient inspiratory and expiratory phases correctly, thereby creating an elevated discomfort for the patient.

With the necessity to calculate the actual leak, the triggering system may inadvertently cause initiated inspiratory triggers due to a flow change caused by, for example, system artifacts such as chest wall elastic recoils, sudden compliance changes in humidifiers, or patient circuits, etc. There have been several systems which measure and attempt to estimate these artifacts during a trigger calculation to avoid inadvertent inspiratory triggering. However, such estimations are not always accurate.

Thus, some of the example embodiments presented herein are directed towards a system, and corresponding method, for calculating an amount of energy associated with an inspiratory phase of breathing. Thus, at the start of an inspiration, samples of the breathing gas flow, breathing gas pressure and breathing gas temperature may be obtained. The sampled and collected values are then used to calculate energy during inspiration.

Calculating the delivered energy during the inspiratory phase allows a calculation of a decay factor which may be applied to a triggering system. The trigger system supplies a trigger which induces a phase shift in a breathing cycle of air supplied by the mechanical ventilator. The phase shift is between an inspiratory and expiratory phase of breathing. The decay factor may adjust the time in which the trigger is provided therefore providing synchronization between the air supplied by the mechanical ventilator and the breathing needs of the patient.

At least one example advantage of the example embodiments presented herein is the ability to calculate a breathing phase trigger without the need of de-pressurization or leakage calculations. Another example advantage of the example embodiments presented herein is the ability to provide a breathing phase trigger which may be dynamic. The breather phase trigger may be dynamic with respect to different patients as well as with respect to the varying breathing needs of a particular patient.

Accordingly, some of the example embodiments are directed towards a method, in a mechanical ventilator, for ventilation synchronization. The method comprises receiving, from a flow sensor, a mass flow signal. The method further comprises receiving, from a pressure sensor, a pressure signal. The method also comprises calculating a total amount of energy during an inspiratory phase of breathing based, at least in part, on the pressure and mass flow signal. The method further comprises determining a decay factor based, in-part, on the total amount of energy. The method also comprises applying the decay factor, during an estimated time slot, to an inspiratory triggering system. The inspiratory trigger system provides a control signal altered according to the decay factor, such that a breathing phase of the mechanical ventilator is synchronized, or substantially synchronized, with a breathing phase of a patient.

Some of the example embodiments are directed towards a computer program product, comprising a computer usable medium having a computer readable program code embodied therein. The computer readable program code is adapted to be executed to implement the method for ventilation synchronization described above.

Some of the example embodiments are directed towards a decay unit, the decay unit being comprised or associated with a mechanical ventilator. The decay unit is configured for ventilation synchronization. The decay unit comprises interface circuitry configured to receive, from a flow sensor, a mass flow signal. The interface circuitry is further configured to receive, from a pressure sensor, a pressure signal. The decay unit further comprises processing circuitry configured to calculate a total amount of energy during an inspiratory phase of breathing, based, at least in part, on the pressure and mass flow signal. The processing circuitry is further configured to determine a decay factor based, in-part, on the total amount of energy. The processing circuitry is also configured to apply the decay factor, during an estimated time slot, to an inspiratory triggering system. The inspiratory triggering system provides a control signal altered according to the decay factor, such that a breathing phase of the mechanical ventilator is synchronized, or substantially synchronized, with a breathing phase of a patient.

DEFINITIONS

Ventilation is the mechanical process of taking air into the airways and lungs and expelling air from the lungs into the atmosphere.

Inspiration is a result of the contraction of the diaphragm muscle, which lowers towards the abdomen. Contraction of the diaphragm increases the size of the chest cavity. Contraction of the intercostal muscles during inspiration increases the chest volume by moving the ribs upwards and outwards. Also the chest wall increases in size during inspiration so there is a greater force pulling outward on the pleura (a thin membrane lining the outer surface of the lung) and the pressure inside it becomes negative. This decrease in pleural pressure causes the pressure inside the alveoli to become more negative, for example, below mouth pressure. This pressure difference between the mouth and the alveoli causes air to move down from the mouth to the alveoli.

Expiration is usually passive due to the relaxation of the diaphragm and intercostal muscles.

BRIEF DESCRIPTION OF THE DRAWINGS

The foregoing will be apparent from the following more particular description of the example embodiments, as illustrated in the accompanying drawings in which like reference characters refer to the same parts throughout the different views. The drawings are not necessarily to scale, emphasis instead being placed upon illustrating the example embodiments.

DETAILED DESCRIPTION

In the following description, for purposes of explanation and not limitation, specific details are set forth, such as particular components, elements, techniques, etc. in order to provide a thorough understanding of the example embodiments. However, it will be apparent to one skilled in the art that the example embodiments may be practiced in other manners that depart from these specific details. In other instances, detailed descriptions of well-known methods and elements are omitted so as not to obscure the description of the example embodiments. The terminology used herein is for the purpose of describing the example embodiments and is not intended to limit the embodiments presented herein.

Figure 1:
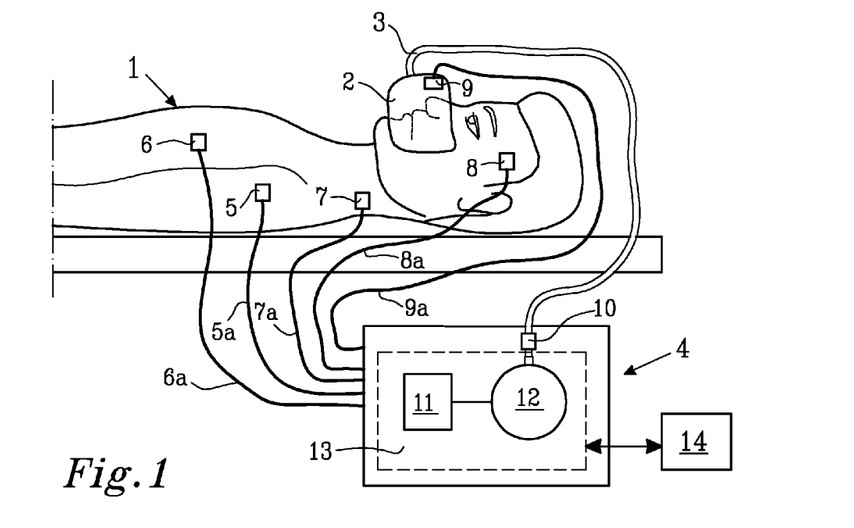
FIG. 1 is a schematic depiction of a ventilatory system, according to some of the example embodiments presented herein.

Some of the example embodiments may be directed towards providing an improved means of synchronization between the breathing phases of gas supplied by a mechanical ventilator and the breathing demands of a patient. FIG. 1 illustrates an example of a mechanical ventilation system used for the treatment of hypoventilation disorders, which may incorporate the example embodiments presented herein. The example ventilation system comprises a mechanical ventilator 4 supplying pressurized breathing gas, tubing 3 for guiding breathing gas to the patient 1 and a breathing mask 2 for administrating the breathing gas to the patient 1. The mask 2 can be a face mask covering both the mouth and nose or a nasal mask covering only the nose or nostrils depending on the patients needs. It can also be a hood covering the complete head or body of the patient. The breathing gas supplied to the patient may be any suitable gas composition for breathing purposes as understood in the art. It should also be appreciated that the breathing gas may be dependent on the physiological status of the patient.

The mechanical ventilation system may also comprise any number of sensors or sensing means 5-9 for determining the physiological status of the patient 1. It should be appreciated that the sensing means 5-9 may be any form of sensor utilized to measure any form of status known in the art. It should further be appreciated that the number of sensors connected to the mechanical ventilator may be one or more.

The example provided by FIG. 1 particularly highlights three types of sensors. Specifically, a breathing mass flow sensor 11, a breathing gas pressure sensor 12 and a breathing gas temperature sensor 10. It should be appreciated that the locations of the sensors provided in FIG. 1 are merely an example. These sensors may be located within, or in electronic communication with, a processing unit 13.

The pressure or flow from the ventilator 4 is controlled by the processing unit 13 as shown in FIG. 1. The processing unit 13 may comprise a computer program or system that measures one or several input parameters via connection means 5a, 6a, 7a, 8a, and 9a obtained from the patient 1. The input parameters may be utilized in describing the physiological status of the patient and pressure/flow data indicative of breathing gas system configuration and status.

These input parameters may be, for example, flow or pressure signals, data obtained from EEG, EMG, EOG, and ECG measurements, $O_2$ and/or $CO_2$ measurements in relation to the patient, body temperature, blood pressure, SpO2 (oxygen saturation), eye movements, and sound measurements. It should be understood that the example embodiments are not limited to the above mentioned input parameters and that any other input parameters may be used.

It should be appreciated that the depicted locations of the sensing means and connection means are provided merely as examples and are in no way limiting to the example embodiments provided herein. For example, the flow signal may be measured at either the mask location or close to the mechanical ventilator or at both locations in order to deduce a differential signal if this is required. Furthermore, the flow sensor 11 may be located at several different positions, for example, in the breathing air tubing 3 at any suitable position, such as close to the mechanical ventilator apparatus (or even within the ventilator housing) or in the vicinity of the mask.

According to some of the example embodiments, only the breathing gas flow, pressure and temperature are used in the synchronization process and thus are the parameters measured. However, it should be appreciated that other signals, in addition or instead of, the flow and pressure signals may be used in the synchronization process depending on the algorithm or system used for determining an energy content of the obtained signals, as will be discussed in further detail below.

The ventilator 4 may further comprise a triggering system 14 which may be configured to provide a trigger for shifting a breathing phase of gas supplied by the ventilator. It should be appreciated that the location of the triggering system 14 is provided merely as an example. The triggering system may be located within the processing unit 13 or the triggering system may be in communication with the processing unit.

In operation, emphasis is placed on the synchronization of breathing gas supplied by the mechanical ventilator 4 and the breathing needs of the patient 1. An asynchrony between the mechanical ventilator and the patient may result in the suffocation of the patient. Thus, triggering systems are utilized to provide a trigger for the mechanical ventilator to shift a current phase of the breathing gas supplied to the patient. Thus, upon receiving the trigger, the mechanical ventilator may shift the phase of the breathing gas to an inspiratory or expiratory phase.

When inspiration phase is terminated and ventilator device 4 enters into expiratory phase the acquired value of inspired energy is diminished linearly or by any other waveform diminishing function, towards zero to allow for next cycle to start with an inspiratory trigger. The duration of the diminishing function is controlled by a decay factor. During the decrease of the inspired energy value the inspirational trigger will be increasing in sensitivity.

Independent of which trigger is used to trigger the inspiratory or expiratory phase, the example embodiments presented herein utilize the total energy during a breathing cycle for determining when such a trigger is allowed to trigger the ventilator to start a new inspiratory or expiratory phase. The synchronization is related to the accumulated energy content as measured using signals from, for example, the mass flow and pressure of breathing gas delivered to the patient. Furthermore, gas leakage in the system may be compensated for in order to relate the energy content to that received by the patient. The gas leakage may be compensated through providing a more precise and dynamic breathing phase trigger, according to some of the example embodiments presented herein. The trigger provides a supplied breathing gas which is more closely matched to a patient's breathing needs. Thus, through the calculations of the dynamic trigger, the leakage is reduced.

The trigger is allowed to start first when the total accumulated energy during a breathing cycle is in equilibrium, for example, the same energy of the breathing gas delivered to the patient during inhalation has been received from the patient during the exhalation. This may be seen as a zero energy state, excluding any leakage. It should be appreciated that the ventilator apparatus may have hardware or software means (not shown) for adjusting trigger levels for both inhalation and exhalation phases separately.

According to some of the example embodiments, a trigger signal supplied to the mechanical ventilator 4 may be adjusted based on a decay factor. The adjustment is provided in order to improve the synchronization between the breathing gas supplied by the mechanical ventilator and the breathing needs of the patient.

According to some of the example embodiments, the processing unit 13 calculates, in response to the patient's inspirational effort, a total amount of energy during the inspiratory phase of breathing. According to some of the example embodiments, the total amount of energy is calculated by summing a total amount of kinetic energy and a total amount of static energy. Such a summation is described in the equation below:

$$E_{INSP} = \dot{m}\left(\frac{p}{\rho} + \frac{V^2}{2} + gh\right) \quad \text{Equation 1}$$

where p is the pressure, ρ is the density of the gas, V is the velocity of breathing gas, g is the acceleration of gravity, and h is the current height or elevation of the patient or breathing gas. A total amount of static energy may be represented by:

$$E_{STATIC} = \dot{m}\left(\frac{p}{\rho}\right). \quad \text{Equation 2}$$

According to some of the example embodiments, the total amount of static energy may be derived from the pressure signal provided by the pressure sensor 12. Thus, the value of the pressure signal, obtained during the inspiratory phase of breathing, may be equivalent to the total amount of static energy during the inspiratory phase.

According to some of the example embodiments, the total amount of kinetic energy may be represented by:

$$E_{KINETIC} = \dot{m}\left(\frac{V^2}{2}\right). \quad \text{Equation 3}$$

The total amount of kinetic energy may be calculated from the flow or mass flow signal provided by the flow sensor 11. In calculating the total amount of kinetic energy, the mass flow signal is divided by a time period. This division results in a volume of air utilized in the inspiratory phase of breathing. According to some of the example embodiments, the time period utilized in the division is a constant value which is dependent on the design of the mechanical ventilator.

The obtained volume is thereafter divided by a diameter of the breathing tube 3 supplying the breathing air to the patient. The division of the volume results in a flow speed or velocity of the breathing gas V. Once the velocity of the breathing gas is determined, the total amount of kinetic energy may be determined as described in Equation 3.

Once the total amount of energy during the inspiratory phase is determined, a rate of patient breathing may be calculated. The rate of patient breathing may be based on a patient breathing history and/or at least one patient characteristic. Non-limiting examples of such patient characteristics may be a patient's sex, age and medical history.

Once the rate of patient breathing is determined, a decay factor, which is to be applied to an inspiration phase trigger, is determined by dividing the total amount of energy by the rate of patient breathing. The determined decay factor is applied to an inspiratory triggering system during an estimated time slot, which may be dependent on the rate of patient breathing. The inspiratory trigger system provides a control signal which is altered according to the decay factor. The control signal is utilized to provide a triggering of a breathing phase of the mechanical ventilator such that the ventilator is synchronized, or substantially synchronized, with a breathing phase of the patient.

According to some of the example embodiments, a period of the decay factor is less than a total amount of inspiratory breathing time and less than the total amount of energy of the inspiratory breathing time divided by a predetermined constant. According to some of the example embodiments, the predetermined constant may be determined by be determined by patient characteristics, for example a time constant associated with a patient's lung. According to some of the example embodiments, the estimated time slot in which the decay factor is supplied to the triggering system may be dependent on the rate of patient breathing.

Figure 2:
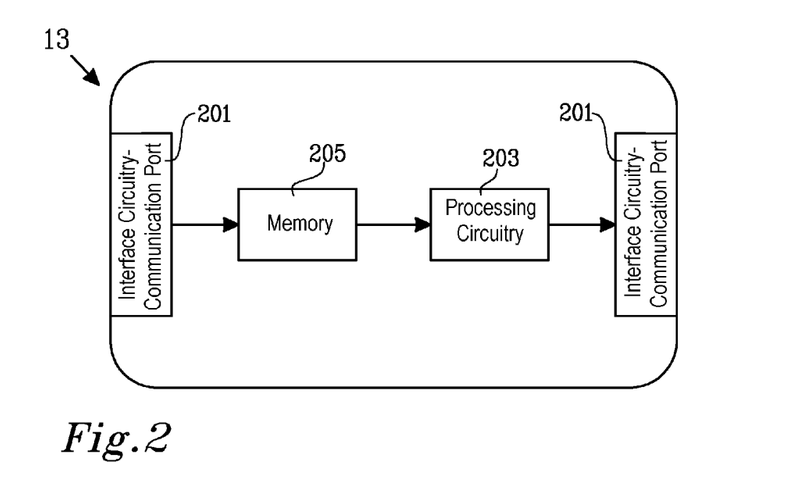
FIG. 2 is a schematic block diagram of a processing unit of the ventilatory system of FIG. 1, according to some of the example embodiments presented herein.

FIG. 2 illustrates an example node configuration of the processing unit 13, which may be configured to utilize some of the example embodiments disclosed herein. The processing unit 13 may comprise interface circuitry or a communication port 201 that may be configured to receive and/or transmit measured data and/or instructions. It should be appreciated that the interface circuitry or communication port 201 may be comprised as any number of transceiving, receiving, and/or transmitting units or circuitry. It should further be appreciated that the interface circuitry or communication 201 may be in the form of any input/output communications port known in the art.

The processing unit 13 may also comprise a processing unit or circuitry 203 which may be configured to determine a trigger or decay factor to be supplied to the trigger. The processing circuitry 203 may be any suitable type of computation unit, e.g. a microprocessor, digital signal processor (DSP), field programmable gate array (FPGA), or application specific integrated circuit (ASIC), or any other form of circuitry.

The processing unit 13 may further comprise a memory unit or circuitry 205 which may be any suitable type of computer readable memory and may be of volatile and/or non-volatile type. The memory 205 may be configured to store received, transmitted, and/or measured data, device parameters and/or executable program instructions.

It should be appreciated that care may be taken in how sampled data is processed, for example filtering or averaging functions, to reduce noise and other external or internal signal disturbances. It should be appreciated that any form of signal processing means may be utilized by the processing unit or processing circuitry in order to improve signal quality. Non-limiting examples of such signal processing means may be low-pass filtering techniques, or other filtering solutions, different averaging solutions, and other more complex signal processing steps such as Fourier analysis. These different "noise" reducing solutions may be implemented either as hardware solutions in the signal path or as software solutions after sampling the signals. The software solutions may be implemented in the processing unit of the ventilator apparatus or as a separate signal sampling unit (not shown) preprocessing data.

Figure 3:
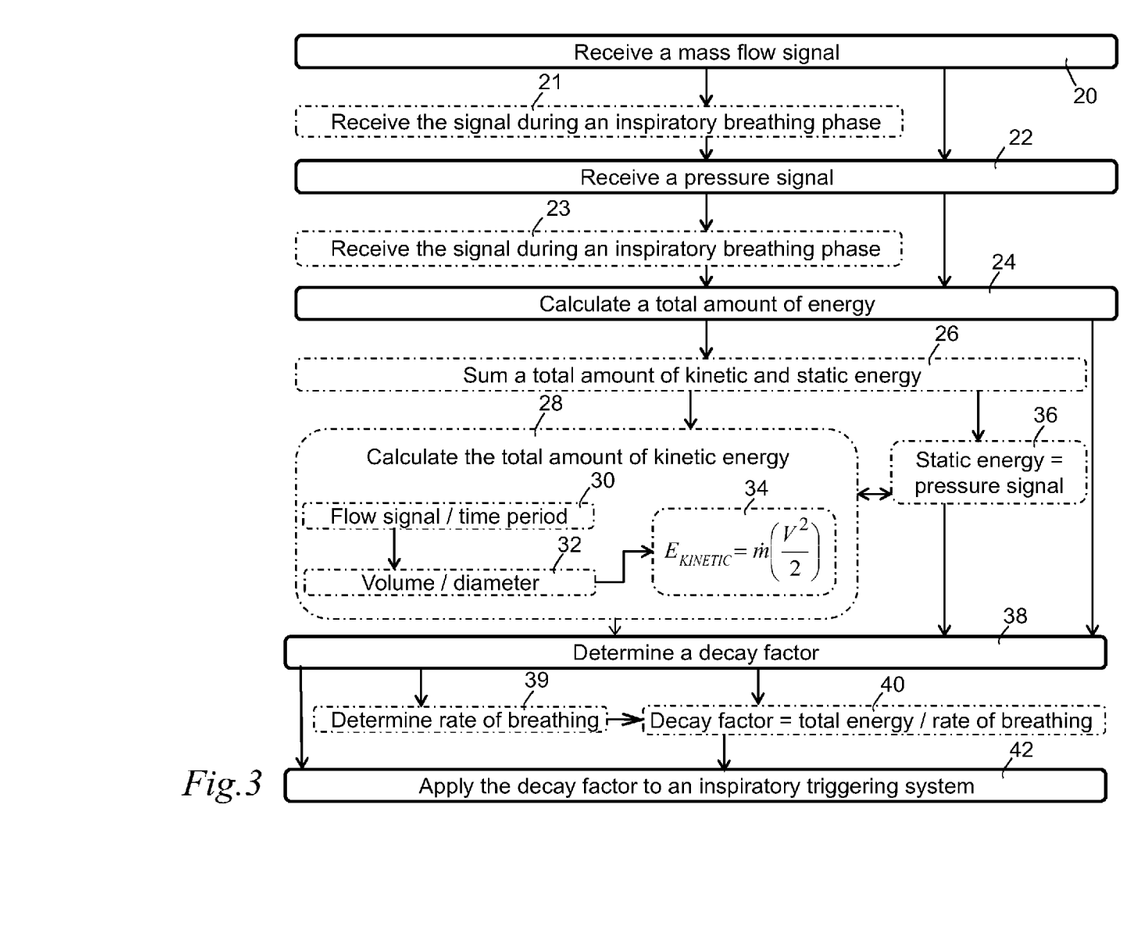
FIG. 3 is a flow diagram of example operations which may be taken by the processing unit of FIG. 2, according to some of the example embodiments presented herein.

FIG. 3 is a flow diagram depicting example operations which may be taken by the processing unit 13 of FIG. 2 in the providing of synchronization between the breathing gas supplied by the mechanical ventilator 4 and the breathing needs of a patient 1. It should also be appreciated that FIG. 3 comprises some operations which are illustrated with a solid border and some operations which are illustrated with a dashed border. The operations which are comprised in a solid border are operations which are comprised in the broadest example embodiment. The operations which are comprised in a dashed border are example embodiments which may be comprised in, or a part of, or are further operations which may be taken in addition to the operations of the boarder example embodiments. It should be appreciated that these operations need not be performed in order. Furthermore, it should be appreciated that not all of the operations need to be performed. The example operations may be performed in any order and in any combination.

Operation 20

The processing unit 13 is configured to receive 20, from a flow sensor 11, a mass flow signal. The interface circuitry 201 is configured to receive the mass flow signal from the mass flow sensor 11.

Example Operation 21

According to some of the example embodiments, the receiving 20 may further comprise receiving 21 the mass flow signal during an inspiratory breathing phase of the mechanical ventilator. The interface circuitry 201 may be configured to receive the mass flow signal during the inspiratory breathing phase of the mechanical ventilator. It should be appreciated that the example embodiments described herein may also be utilized for supplying a trigger to initiate an expiratory breathing phase. In such case, the mass flow signal may be obtained during an expiratory breathing phase.

Operation 22

The processing unit 13 is further configured to receive 22, from a pressure sensor 12, a pressure signal. The interface circuitry 201 is configured to receive, from the pressure sensor, the pressure signal.

Example Operation 23

According to some of the example embodiments, the receiving 22 may further comprise receiving 23 the pressure signal during an inspiratory breathing phase of the mechanical ventilator. The interface circuitry 201 may be configured to receive the pressure signal during the inspiratory breathing phase of the mechanical ventilator. It should be appreciated that the example embodiments described herein may also be utilized for supplying a trigger to initiate an expiratory breathing phase. In such case, the pressure signal may be obtained during an expiratory breathing phase.

Operation 24

The processing unit 13 is further configured to calculate 24 a total amount of energy during an inspiratory phase of breathing based, at least in part, on the pressure and mass flow signals. The processing circuitry 203 is configured to calculate the total amount of energy during the inspiratory phase of breathing based, at least in part, on the pressure and mass flow signals.

Example Operation 26

According to some of the example embodiments, the calculating 24 may further comprising summing 26 a total amount of kinetic energy and a total amount of static energy. The kinetic energy may be derived from the mass flow signal and the static energy may be derived from the pressure signal. The processing circuitry may be configured to sum the total amount of kinetic energy and the total amount of static energy.

Example Operation 28

According to some of the example embodiments, the calculating 24 and summing 26 may further comprise calculating 28 the total amount of kinetic energy. The processing circuitry 203 may be configured to calculate the total amount of kinetic energy.

Example Operation 30

According to some of the example embodiments, the calculating 28 may further comprise dividing 30 the mass flow signal by a time period resulting in a volume. The processing circuitry 203 may be configured to divide the mass flow signal by the time period resulting in the volume. According to some of the example embodiments, the time period may be a constant value depending on a design of the mechanical ventilator.

Example Operation 32

According to some of the example embodiments, the calculating 28 may further comprise dividing 32 the volume by a diameter of the breathing tube 3 supplying air to the patient. The result of the division is a flow speed V. The processing circuitry may be configured to divide the volume by the diameter of the breathing tube supplying air to the patient.

Example Operation 34

According to some of the example embodiments, the calculating 28 may further comprise determining 34 the total amount of kinetic energy according to the formula provided in Equation 3. The processing circuitry 203 may be configured to determine the total amount of kinetic energy according to the formula provided in Equation 3.

Example Operation 36

According to some of the example embodiments, the calculating 24 and the summing 26 may further comprise determining 36 the total amount of static energy being equal to the pressure signal. The processing circuitry 203 may be configured to determine the total amount of static energy being equal to the pressure signal.

Operation 38

The processing unit 13 is further configured to determine 38 a decay factor based, at least in part, on the total amount of energy. The processing circuitry 203 is configured to determine the decay factor based, at least in part, on the total amount of energy.

Example Operation 39

According to some of the example embodiments, the processing unit 13 may be further configured to determine 39 a rate of patient breathing based on a patient history and/or at least one patient characteristic. The processing circuitry 203 may be configured to determine the rate of patient breathing based on the patient history and/or at least one patient characteristic. Non-limiting examples of such patient characteristics may be a patient's age, sex, medical history, and/or any other form of data known in the art which may have an effect on lung mechanics.

Example Operation 40

According to some of the example embodiments, the determining 38 may further comprise calculating 40 a division of the total amount of energy over the rate of patient breathing. The result of the division is the decay factor. The processing circuitry 203 may be configured to calculate the division of the total amount of energy over the rate of patient breathing.

Operation 42

The processing unit 13 is further configured to apply the decay factor, during an estimated time slot, to an inspiratory triggering system. The inspiratory triggering system 14 provides a control signal altered according to the decay factor such that a breathing phase of the mechanical ventilator is synchronized, or substantially synchronized, with a breathing phase of the patient. The processing circuitry 203 is configured to apply the decay factor, during the estimated time slot, to the inspiratory triggering system.

According to some of the example embodiments, a period of the decay factor is less than a total amount of inspiratory breathing time and less than the total amount of inspiratory breathing time divided by a predetermined constant. According to some of the example embodiments the predetermined constant may be dependent on a patient characteristic, for example, a time constant of a lung. According to some of the example embodiments, the predetermined constant may be 2 or 3. According to some of the example embodiments, the estimated time slot is dependent on the rate of patient breathing. It should be appreciated that the functionality of the triggering system 14 may be provided within the processing unit 13 or the processing circuitry 203. It should also be appreciated that the triggering system 14 may be in communication with the processing unit 13, as illustrated in FIG. 1.

Figure 4:
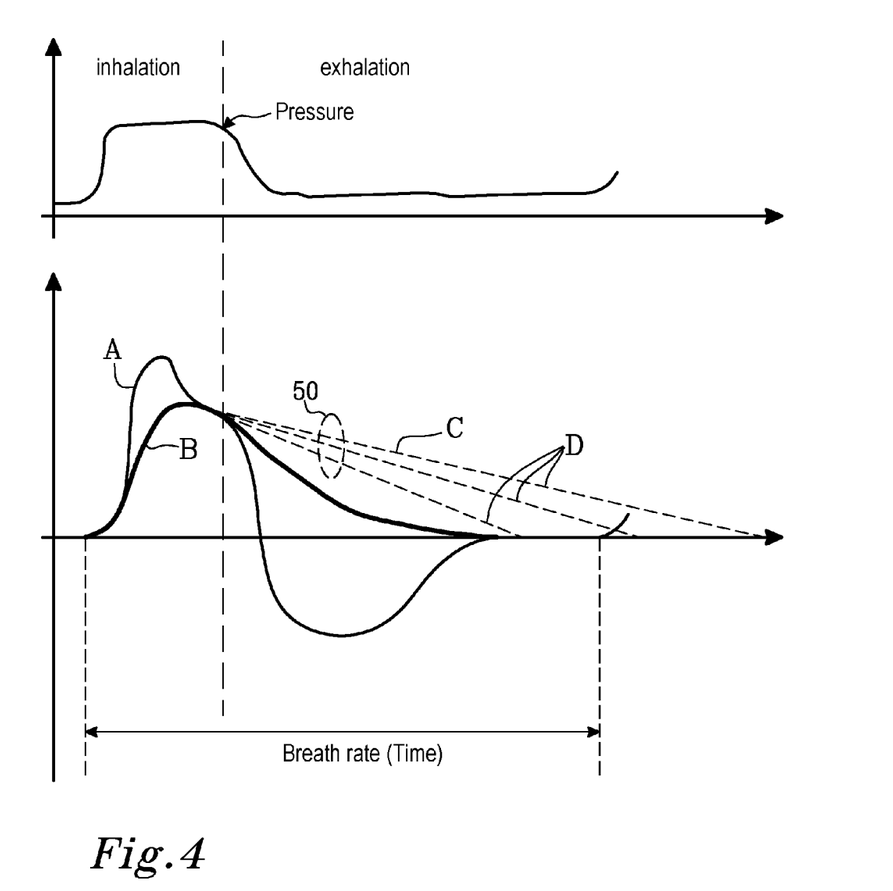
FIG. 4 illustrates pressure, flow and inspired energy data and the effects of an applied control signal or trigger, with respect to a patient's breathing cycle, according to some of the example embodiments presented herein.

FIG. 4 illustrates three data curves associated with one breathing cycle of a patient. The area to the left of the broken line represents the inhalation phase, and the area to the right of the broken line represents the exhalation phase. The topmost curve is a depiction of a pressure curve. The pressure curve illustrates the pressure exerted by the patient during an entire breathing cycle. As illustrated in the pressure curve of FIG. 4, the amount of pressure exerted by the patient increases exponentially during the inhalation phase and drops significantly during the exhalation phase.

The bottommost graph illustrates flow A and energy B curves associated with the breathing cycle. As illustrated, the breathing flow is at its greatest peak during the inhalation phase and drops during the exhalation phase as the patient is breathing outward. Similarly, the energy is at its greatest peak during the inhalation phase and drops during the exhalation phase. As explained above, in order to match the breathing needs of a patient with a breathing gas supplied by a mechanical ventilator, a triggering from the inhalation phase and the exhalation phase is provided (e.g., a trigger to begin the decrease of the provided flow). Various triggers or decay factors 50 may be supplied to a control signal. The control signal C is derived from the peak inspired energy, whereby the inclination D of the control signal may be determined by the decay factor, as described above. The control signal is fed into the triggering mechanism as an attenuator to enhance synchronization to a patient's breathing rhythm. The control signal may in-turn be used to alter the flow in order to adjust the moment when the exhalation breathing phase begins. The triggering may be provided as described in relation to FIG. 3. It should be appreciated that the triggering may be provided in a dynamic fashion with respect to a particular patient and with respect to the different needs of that patient as the breathing cycle for that particular patient may change with time.

It should be appreciated that there are many types of ventilation modes where the above described method and apparatus may find its application including but not limited to:

1. Continuous positive airway pressure (CPAP): this is a spontaneous breathing mode—no mandatory breaths are delivered.
2. Synchronized intermittent mandatory ventilation (SIMV): mandatory breaths are delivered at a set rate with volume control or pressure control. Between the mandatory breaths the patient is allowed to breathe spontaneously.
3. Assist control mechanical ventilation (ACMV),
4. Pressure control ventilation (PCV),
5. Pressure support ventilation (PSV): the patient's inspiratory effort is assisted by the ventilator at a preset level of inspiratory pressure. Inspiration is triggered and cycled by patient effort.
6. Proportional assist ventilation (PAV), and
7. Volume assured pressure support (VAPS)

The example embodiments presented herein may also be used for exercising patients or healthy persons in order to increase their lung capacity which may have been reduced for some reason, for example, after a surgical procedure, accident, or by a medical illness. By exercising, it is possible to reduce risks for patients with reduced breathing capacities. It may also be possible to use the example embodiments presented herein in a weaning processes where patients connected to a respirator train with a system according to the example embodiments in order to remove the need for the respirator. This is a gradual process where the patient's diaphragm is trained until the patient is strong enough to breathe without the help from a respirator.

It should be appreciated that the utilization of the example embodiments allow for the work of breathing for a patient to be reduced and greater comfort in breathing assistance may be provided. The example embodiments described herein may be used for treatment of many other different forms of ventilatory failure events or hypoventilation events, and treatment may be done both at home and in the clinical environment. Examples of groups of breathing disorders include, but are not limited to, breathing disorders during sleep, obstructive lung diseases (COPD), neuromuscular disorders, neurological disorders, chest wall disorders, and more. It should further be appreciated that the example embodiments described herein may be utilized to provide a trigger in order to shift to an inspiratory or expiratory breathing phase of the mechanical ventilator.

The description of the example embodiments provided herein have been presented for purposes of illustration. The description is not intended to be exhaustive or to limit example embodiments to the precise form disclosed, and modifications and variations are possible in light of the above teachings or may be acquired from practice of various alternatives to the provided embodiments. The examples discussed herein were chosen and described in order to explain the principles and the nature of various example embodiments and its practical application to enable one skilled in the art to utilize the example embodiments in various manners and with various modifications as are suited to the particular use contemplated. The features of the embodiments described herein may be combined in all possible combinations of methods, apparatus, modules, systems, and computer program products. It should be appreciated that the example embodiments presented herein may be practiced in any combination with each other.

It should be noted that the word "comprising" does not necessarily exclude the presence of other elements or steps than those listed and the words "a" or "an" preceding an element do not exclude the presence of a plurality of such elements. It should further be noted that any reference signs do not limit the scope of the claims, that the example embodiments may be implemented at least in part by means of both hardware and software, and that several "means", "units" or "devices" may be represented by the same item of hardware.

The various example embodiments described herein are described in the general context of method steps or processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

In the drawings and specification, there have been disclosed exemplary embodiments. However, many variations and modifications can be made to these embodiments. Accordingly, although specific terms are employed, they are used in a generic and descriptive sense only and not for purposes of limitation, the scope of the embodiments being defined by the following example embodiments.

The invention claimed is:

1. A method, in a mechanical ventilator, for ventilation synchronization, the method comprising:
   receiving, from a flow sensor, a mass flow signal;
   receiving, from a pressure sensor, a pressure signal;
   calculating a total amount of energy during an inspiratory phase of breathing based, at least in part, on the pressure and mass flow signals;
   determining a decay factor based, in-part, on the total amount of energy; and
   applying said decay factor, during an estimated time slot, to an inspiratory triggering system, said inspiratory trigger system providing a control signal altered according to said decay factor, such that a breathing phase of the mechanical ventilator is synchronized, or substantially synchronized, with a breathing phase of a patient.

2. The method of claim 1, wherein the receiving further comprises receiving the mass flow signal during an inspiratory breathing phase.

3. The method of any of claim 1, wherein the receiving further comprises receiving the pressure signal during an inspiratory breathing phase.

4. The method of any of claim 1, wherein the calculating further comprises summing a total amount of kinetic energy and a total amount of static energy, wherein the kinetic energy is derived from the mass flow signal and the static energy is derived from the pressure signal.

5. The method of claim 4, further comprising calculating the total amount of kinetic energy.

6. The method of claim 5, wherein the calculating further comprises dividing the mass flow signal by a time period resulting in a volume.

7. The method of claim 6, wherein the time period is a constant value dependent on a design of the mechanical ventilator.

8. The method of claim 6, wherein the calculating further comprises dividing the volume by a diameter of a breathing tube supply air to a patient resulting in a flow speed.

9. The method of claim 8, wherein the calculating further comprises determining the total amount of kinetic energy according to the following formula:

$$KE = \frac{mV^2}{2},$$

where KE is the total amount of kinetic energy, m is a mass of patient inhalation air, and V is the flow speed of said patient inhalation air.

10. The method of claim 4, further comprising determining the total amount of static energy being equal to the pressure signal.

11. The method of claim 1, further comprising determining a rate of patient breathing based on a patient breathing history and/or at least one patient characteristic.

12. The method of claim 11, wherein the determining the decay factor further comprises calculating a division of the total amount of energy over the rate of patient breathing.

13. The method of claim 1, wherein a period of the decay factor is less than a total amount of inspiratory breathing time and less than the total amount of inspiratory breathing time divided by a predetermined constant.

14. The method of claim 11, wherein the estimated time slot is dependent on the rate of patient breathing.

15. A processing unit, said processing unit being comprised or associated with a mechanical ventilator, for ventilation synchronization, the processing unit comprising:
   interface circuitry configured to receive, from a flow sensor, a mass flow signal;
   the interface circuitry further configured to receive, from a pressure sensor, a pressure signal;
   processing circuitry configured to calculate a total amount of energy during an inspiratory phase of breathing, based, at least in part, on the pressure and mass flow signals;
   the processing circuitry further configured to determine a decay factor based, in-part, on the total amount of energy; and
   the processing circuitry configured to apply said decay factor, during an estimated time slot, to an inspiratory triggering system, said inspiratory triggering system providing a control signal altered according to said decay factor, such that a breathing phase of the mechanical ventilator is synchronized, or substantially synchronized, with a breathing phase of a patient.

16. The processing unit of claim 15, wherein the interface circuitry is further configured to receive the mass flow signal during an inspiratory breathing phase.

17. The processing unit of claim 15, wherein the interface circuitry is further configured to receive the pressure signal during an inspiratory breathing phase.

18. The processing unit of claim 15, wherein the processing circuitry is further configured to calculate the total amount of energy via a sum of a total amount of kinetic energy and a total amount of static energy, wherein the kinetic energy is derived from the mass flow signal and the static energy is derived from the pressure signal.

19. The processing unit of claim 18, wherein the processing circuitry is further configured to calculate the total amount of kinetic energy.

20. The processing unit of claim 19, wherein the processing circuitry is further configured to divide the mass flow signal by a time period resulting in a volume.

21. The processing unit of claim 20, wherein the time period is a constant value dependent on a design of the mechanical ventilator.

22. The processing unit of claim 20, wherein the processing circuitry is further configured to divide the volume by a diameter of a breathing tube supply air to a patient resulting in a flow speed.

23. The processing unit of claim 22, wherein the processing circuitry is further configured to determine the total amount of kinetic energy according to the following formula:

$$KE = \frac{mV^2}{2},$$

where KE is the total amount of kinetic energy, m is a mass of patient inhalation air, and V is the flow speed of said patient inhalation air.

24. The processing unit of claim 18, wherein the processing circuitry is further configured to determine the total amount of static energy as being equal to the pressure signal.

25. The processing unit of claim 15, wherein the processing circuitry is further configured to determine a rate of patient breathing based on a patient breathing history and/or at least one patient characteristic.

26. The processing unit of claim 25, wherein the processing circuitry is further configured to determine the decay factor from a division of the total amount of energy and the rate of patient breathing.

27. The processing unit of claim 15, wherein a period of the decay factor is less than a total amount of inspiratory breathing time and less than the total amount of inspiratory breathing time divided by a predetermined constant.

28. The processing unit of claim 25, wherein the estimated time slot is dependent on the rate of patient breathing.

29. A computer program product, comprising a computer usable medium having a computer readable program code embodied therein, said computer readable program code adapted to be executed to implement a method for ventilation synchronization of a mechanical ventilator with a breathing phase of a patient, said method comprising:
- receiving, from a flow sensor, a mass flow signal;
- receiving, from a pressure sensor, a pressure signal;
- calculating a total amount of energy during an inspiratory phase of breathing based, at least in part, on the pressure and mass flow signals;
- determining a decay factor based, in-part, on the total amount of energy; and
- applying said decay factor, during an estimated time slot, to an inspiratory triggering system, said inspiratory trigger system providing a control signal altered according to said decay factor, such that a breathing phase of the mechanical ventilator is synchronized, or substantially synchronized, with the breathing phase of the patient.

* * * * *